(12) United States Patent
Endo et al.

(10) Patent No.: US 10,743,843 B2
(45) Date of Patent: Aug. 18, 2020

(54) INFORMATION PROCESSING APPARATUS, ULTRASONIC IMAGING APPARATUS, AND INFORMATION PROCESSING METHOD

(71) Applicant: CANON KABUSHIKI KAISHA, Tokyo (JP)

(72) Inventors: Takaaki Endo, Urayasu (JP); Ryo Ishikawa, Kawasaki (JP); Kiyohide Satoh, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 473 days.

(21) Appl. No.: 15/625,012

(22) Filed: Jun. 16, 2017

(65) Prior Publication Data

US 2017/0281134 A1 Oct. 5, 2017

Related U.S. Application Data

(63) Continuation of application No. 13/595,434, filed on Aug. 27, 2012.

(30) Foreign Application Priority Data

Aug. 31, 2011 (JP) ................................ 2011-189022
Jul. 4, 2012 (JP) ................................ 2012-150472

(51) Int. Cl.
*A61B 8/08* (2006.01)
*A61B 8/00* (2006.01)
(Continued)

(52) U.S. Cl.
CPC ............ *A61B 8/5223* (2013.01); *A61B 5/055* (2013.01); *A61B 6/032* (2013.01); *A61B 6/4417* (2013.01);
(Continued)

(58) Field of Classification Search
CPC ....... A61B 8/4245; A61B 8/42; A61B 8/5223; A61B 8/461; A61B 5/055; A61B 6/032;
(Continued)

(56) References Cited

U.S. PATENT DOCUMENTS 5,638,819 A 6/1997 Manwaring et al.
7,458,977 B2 12/2008 McGinley et al.
(Continued)

FOREIGN PATENT DOCUMENTS

EP 1525850 A1 4/2005
JP 4028354 A 1/1992
(Continued)

OTHER PUBLICATIONS

Kazhdan, M. et al., "Poisson Surface Reconstruction", Proc. Symposium on Geometry Processing, 2006, pp. 61-70.

*Primary Examiner* — Sanjay Cattungal
(74) *Attorney, Agent, or Firm* — Canon U.S.A., Inc., IP Division

(57) ABSTRACT

An ultrasonic imaging support apparatus for supporting imaging performed by an ultrasonic probe that acquires an ultrasonic image of a subject includes a specification unit configured to specify a position inside the subject in a three dimensional image, an identification unit configured to identify a position on a body surface of the subject based on the specified position, and a display control unit configured to display a position where the ultrasonic image acquired by the ultrasonic probe is captured and the identified position on a display unit.

21 Claims, 13 Drawing Sheets

(51) Int. Cl.
*A61B 5/055* (2006.01)
*A61B 6/03* (2006.01)
*A61B 6/00* (2006.01)
*G01R 33/48* (2006.01)

(52) U.S. Cl.
CPC .......... *A61B 8/0825* (2013.01); *A61B 8/4245* (2013.01); *A61B 8/4416* (2013.01); *A61B 8/461* (2013.01); *A61B 8/463* (2013.01); *A61B 8/483* (2013.01); *A61B 8/54* (2013.01); *G01R 33/4814* (2013.01)

(58) Field of Classification Search
CPC ..... A61B 6/4417; A61B 8/0825; A61B 8/463; A61B 8/483; A61B 8/4416; A61B 8/54; G01S 7/52073; G01R 33/4814
See application file for complete search history.

(56) References Cited

U.S. PATENT DOCUMENTS

| | | |
|---|---|---|
| 7,850,613 B2 | 12/2010 | Stribling |
| 8,926,513 B2 * | 1/2015 | Yao ................. A61B 8/0825 382/128 |
| 2003/0130575 A1 | 7/2003 | Desai |
| 2005/0107695 A1 | 5/2005 | Kiraly et al. |
| 2005/0119569 A1 | 6/2005 | Ohtake |
| 2006/0100521 A1 | 5/2006 | Takeuchi |
| 2006/0241432 A1 | 10/2006 | Herline et al. |
| 2006/0251301 A1 | 11/2006 | McNamara, Jr. et al. |
| 2007/0225553 A1 | 9/2007 | Shahidi |
| 2007/0236514 A1 | 10/2007 | Agusanto et al. |
| 2008/0123910 A1 | 5/2008 | Zhu |
| 2008/0194959 A1* | 8/2008 | Wang ................... A61B 8/0825 600/445 |
| 2008/0208061 A1 | 8/2008 | Halmann |
| 2008/0306384 A1* | 12/2008 | Boctor ................... A61B 8/08 600/443 |
| 2009/0024030 A1 | 1/2009 | Lachaine et al. |
| 2010/0027859 A1 | 2/2010 | Heinlein et al. |
| 2010/0130855 A1 | 5/2010 | Lundberg et al. |
| 2010/0217125 A1* | 8/2010 | Kadokura ........ A61B 5/02007 600/443 |
| 2011/0132094 A1 | 6/2011 | Nakamura et al. |
| 2011/0172526 A1* | 7/2011 | Lachaine ............... A61B 34/20 600/439 |
| 2011/0230759 A1 | 9/2011 | Muller |
| 2012/0007863 A1* | 1/2012 | Endo ..................... A61B 8/13 345/419 |
| 2015/0320391 A1* | 11/2015 | Yao ....................... A61B 8/462 600/424 |

FOREIGN PATENT DOCUMENTS

| | | |
|---|---|---|
| JP | 2005-124712 A | 5/2005 |
| JP | 2008-518684 A | 6/2008 |
| JP | 2008-279272 A | 11/2008 |
| JP | 2009-268735 A | 11/2009 |
| JP | 2011-097985 A | 5/2011 |
| WO | 2006/059668 A1 | 6/2006 |

* cited by examiner

US 10,743,843 B2

INFORMATION PROCESSING APPARATUS, ULTRASONIC IMAGING APPARATUS, AND INFORMATION PROCESSING METHOD

CROSS-REFERENCE TO RELATED APPLICATIONS

This application is a Continuation of co-pending U.S. patent application Ser. No. 13/595,434 filed Aug. 27, 2012, now abandoned, which claims foreign priority benefit of Japanese Patent Applications No. 2011-189022 filed Aug. 31, 2011 and No. 2012-150472 filed Jul. 4, 2012. The disclosures of the above-named applications are hereby incorporated by reference herein in their entirety.

BACKGROUND

Technical Field

The present disclosure relates to an information processing apparatus, an ultrasonic imaging apparatus, and an information processing method.

Description of the Related Art

An ultrasonic image diagnostic apparatus (an ultrasonic imaging apparatus) can non-invasively and simply acquire an image inside an subject, however, it is difficult for the apparatus to image a certain tissue of the subject, and the apparatus has a problem in that an image quality is inferior. Using the image acquired by the ultrasonic image diagnostic apparatus with an image acquired by a magnetic resonance imaging (MRI) apparatus, an X-ray computed tomography apparatus (an X-ray CT apparatus), or a nuclear medicine diagnostic apparatus (a positron emission tomography (PET) apparatus or a single photon emission computed tomography (SPECT) apparatus) allows efficient and accurate diagnosis. For example, a diagnosis is performed in which a target site in the body is previously specified by an MRI image and the target site is imaged and confirmed also by the ultrasonic image diagnostic apparatus.

A technique for appropriately supporting operation in a medical doctor finding a target site using an ultrasonic imaging apparatus is useful to improve an operation efficiency in a medical site, to decrease a burden to a patient, and to be able to realize reduction in cost. For example, there is a display method for displaying, on a body mark, a guide image indicating how to place an ultrasonic probe to image a lesion area. This method reads a guide image according to a lesion area from among a large number of guide images indicating how to place the ultrasonic probe, and combines the guide image with a body mark to display the combined image. In another example, there is a display method for displaying, on a 3D body mark, a graphic indicating a position of a lesion area, a graphic indicating an ultrasonic image plane, and an arrow graphic indicating a direction toward the center position of the lesion area from the ultrasonic image plane. In a still another example, there is a display method for displaying a registered probe mark indicating the position of an ultrasonic probe in the past diagnosis, a current probe mark indicating the position of an ultrasonic probe in the current diagnosis, and a graphic indicating displacement in a coordinate between the registered probe mark and the current probe mark.

SUMMARY

According to some embodiments of the present invention, an ultrasonic imaging support apparatus for supporting imaging performed by an ultrasonic probe that acquires an ultrasonic image of a subject includes a specification unit configured to specify a position inside the subject in a three dimensional image, an identification unit configured to identify a position on a body surface of the subject based on the specified position, and a display control unit configured to display a position where the ultrasonic image acquired by the ultrasonic probe is captured and the identified position on a display unit.

Further features and aspects of the present disclosure will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the embodiments of the present invention.

DESCRIPTION OF THE EMBODIMENTS

Various exemplary embodiments of the invention will be described in detail below with reference to the drawings.

An ultrasonic imaging system, which one of exemplary embodiments of the present invention and is taken as an example, is described below.

Figure 1:
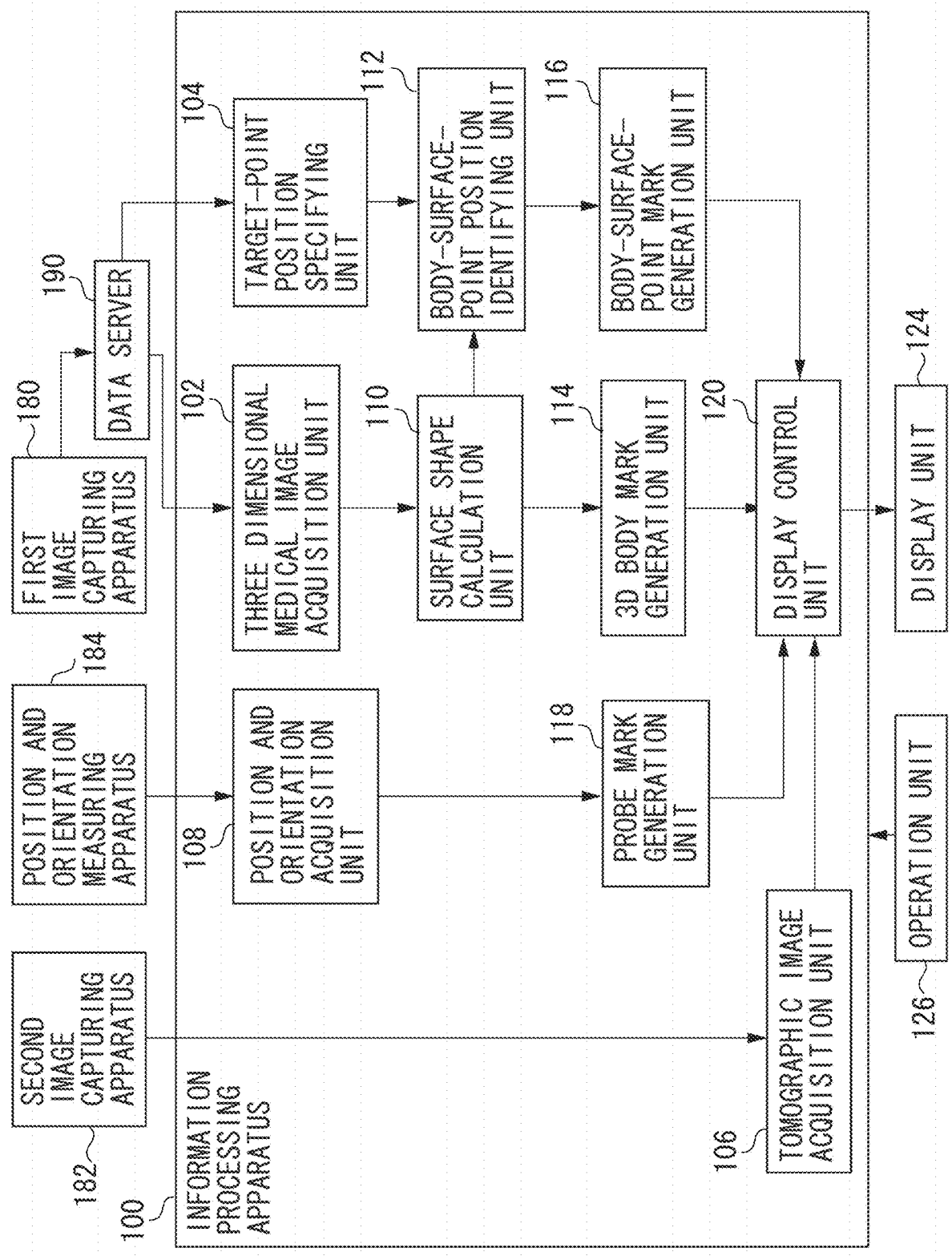
FIG. 1 illustrates a device configuration of an information processing apparatus according to a first exemplary embodiment.

FIG. 1 illustrates a configuration of the ultrasonic imaging system according to an exemplary embodiment. As illustrated in FIG. 1, an information processing apparatus 100 according to the present exemplary embodiment is connected with a second image capturing apparatus 182, a position and an orientation measuring apparatus 184, and a data server 190.

The information processing apparatus 100 according to the present exemplary embodiment calculates the position of a body-surface point extended to the surface of a subject from a target point in a three dimensional medical image in which the subject is captured. The information processing apparatus 100 displays, on a 3D body mark indicating the subject, a graphic (a body-surface-point mark) indicating information about the position of a body-surface point along with a graphic (a probe mark) indicating information about the position of an ultrasonic probe. The present exemplary embodiment describes an example in which the breast of the human body is taken as a subject and the center of a three dimensional area indicating the extension of a lesion (hereinafter referred to as a lesion area) is taken as a target point. The present exemplary embodiment also describes an example where an MRI image in which the breast in the supine position is captured by an MRI apparatus is taken as a three dimensional medical image.

Figure 9:
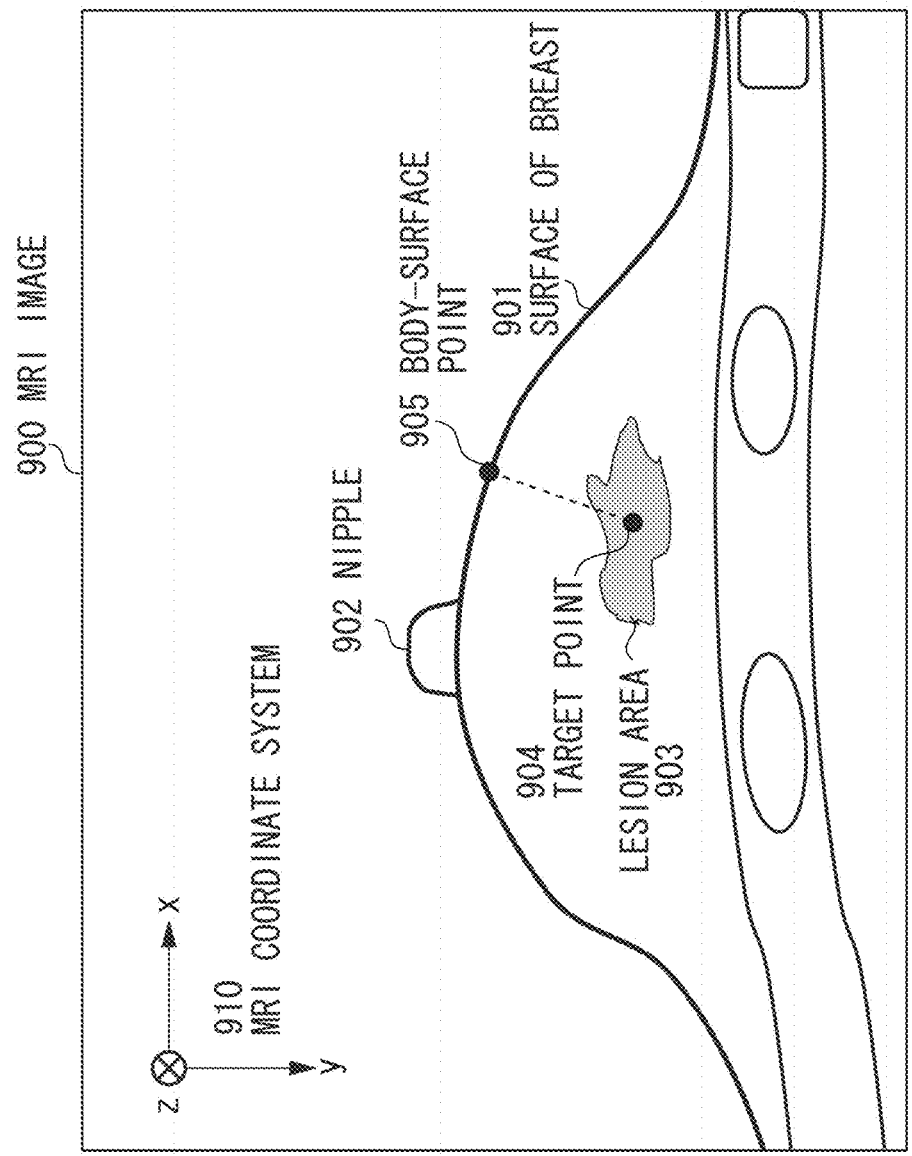
FIG. 9 illustrates an example of an MRI image.

The data server 190 stores an MRI image acquired by capturing the breast in the supine position by the MRI apparatus acting as a first image capturing apparatus 180 and information about the position of the target point in the MRI image. FIG. 9 illustrates an example of the MRI image. An MRI image 900 stored in the data server 190 is input to the information processing apparatus 100 via a three dimensional medical image acquisition unit 102. Information about the position of center of a lesion area 903 (a target point 904) stored in the data server 190 is input into the information processing apparatus 100 via a target-point position specifying unit 104.

Figure 6:
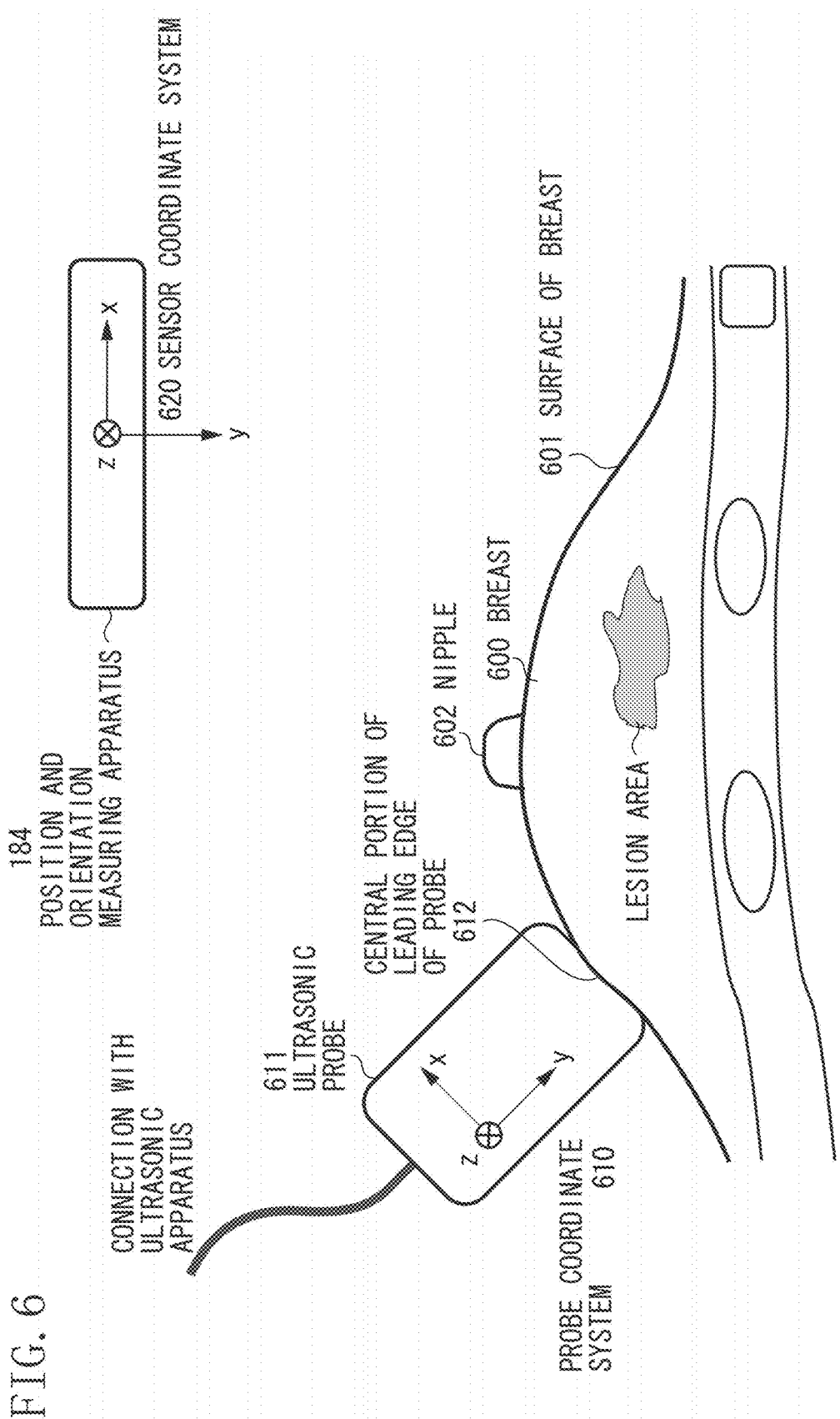
FIG. 6 illustrates a state where the ultrasonic tomographic image of the breast is captured.
Figure 7:
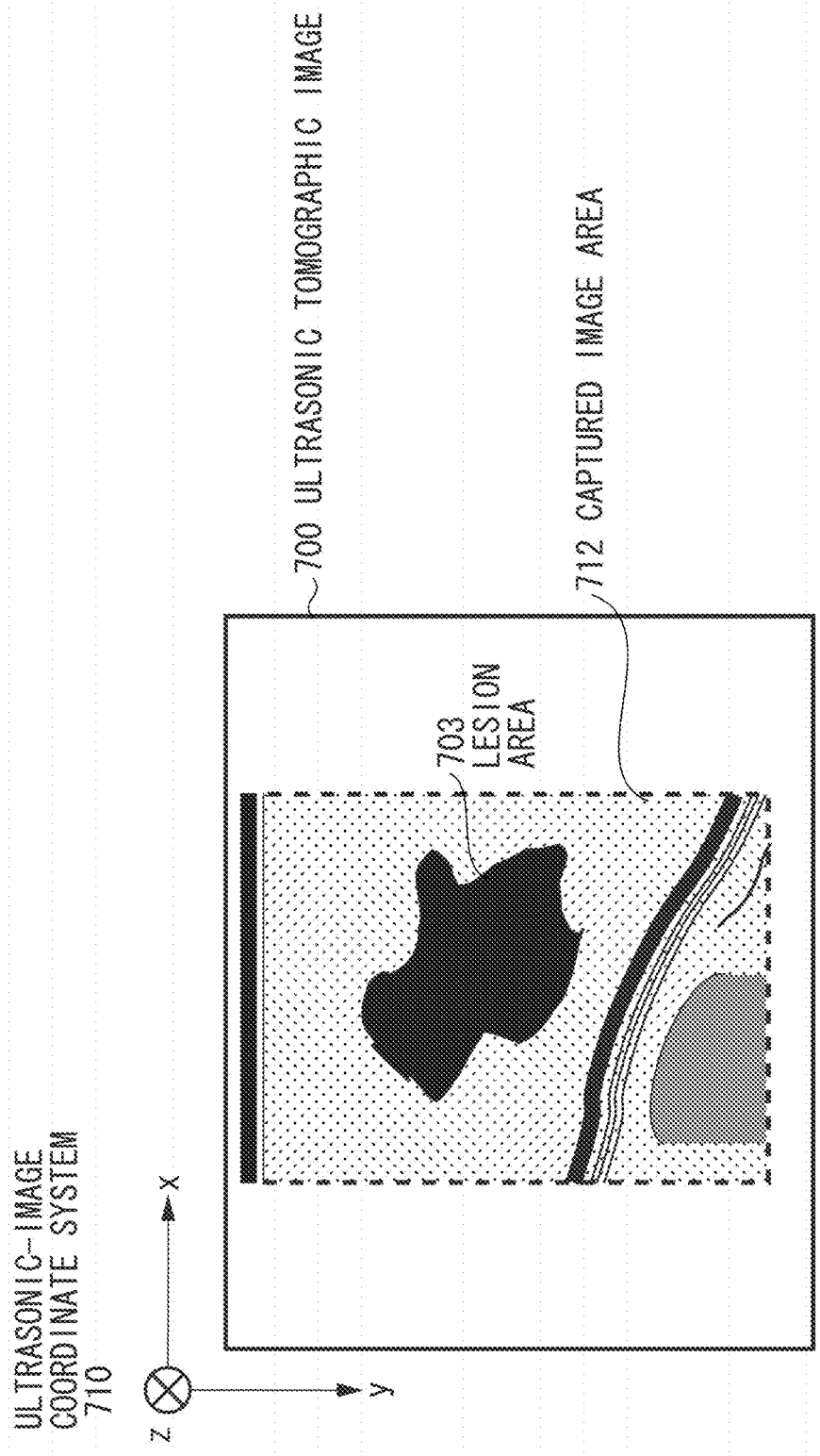
FIG. 7 illustrates an example of an ultrasonic tomographic image.

An ultrasonic apparatus acting as the second image capturing apparatus 182 causes an ultrasonic probe to transmit and receive an ultrasonic signal to capture the breast in the supine position. FIG. 6 illustrates a state where the ultrasonic tomographic image of the breast 600 is captured. FIG. 7 illustrates an example of an ultrasonic tomographic image. The ultrasonic tomographic image 700 acquired by placing an ultrasonic probe 611 on a surface 601 of the breast 600 is sequentially input into the information processing apparatus 100 via a tomographic image acquisition unit 106.

The position and orientation measuring apparatus 184 measures the position and the orientation of the ultrasonic probe 611 with which the ultrasonic apparatus acting as the second image capturing apparatus 182 is provided. The position and orientation measuring apparatus 184 is formed of FASTRAK from Polhemus Inc., in USA, for example, and measures the position and the orientation of the ultrasonic probe 611 in a sensor coordinate system 620 (a coordinate system defined as a standard by the position and orientation measuring apparatus 184). The position and orientation measuring apparatus 184 may be configured at will as long as the position and the orientation of the ultrasonic probe 611 can be measured. The measured position and orientation of the ultrasonic probe 611 are sequentially input into the information processing apparatus 100 via a position and orientation acquisition unit 108.

The information processing apparatus 100 is the one that supports capturing by using the ultrasonic probe for acquiring the ultrasonic image of the subject and includes the following components described below. The three dimensional medical image acquisition unit 102 acquires the MRI image 900 acquired by capturing the subject in the supine position and outputs the MRI image 900 to a surface shape calculation unit 110.

The target-point position specifying unit 104 specifies the position of a target point 904 by storing the coordinate of the target point 904 in a memory based on information about the position of the target-point 904 in the subject input to the information processing apparatus 100 and outputs the information to a body-surface-point position identifying unit 112.

The tomographic image acquisition unit 106 sequentially acquires the ultrasonic tomographic image 700 input to the information processing apparatus 100 and outputs the image to a display control unit 120. The position and orientation acquisition unit 108 sequentially acquires the position and orientation of the probe 611 input to the information processing apparatus 100 and outputs the position and orientation thereof to a probe mark generation unit 118. The surface shape calculation unit 110 calculates shape data on the surface 901 of the breast based on the MRI image 900 and outputs the shape data to the body-surface-point position identifying unit 112 and the 3D body mark generation unit 114.

Figure 8:
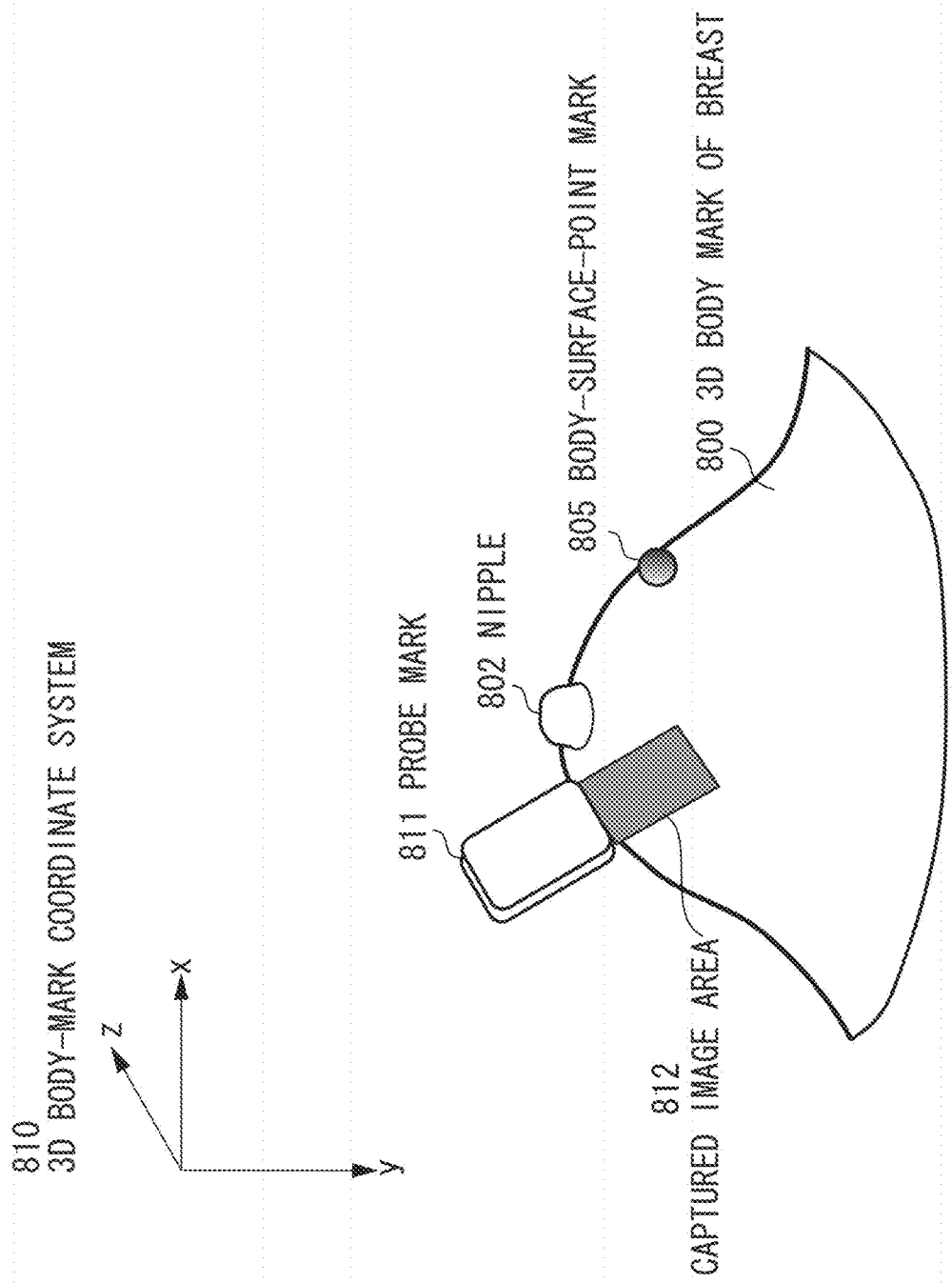
FIG. 8 illustrates an example of a 3D body mark.

The body-surface-point position identifying unit 112 identifies the position of the body-surface point 905 on the body surface of the subject based on the specified target-point 904. Here, the body-surface-point position identifying unit 112 calculates the position of the body-surface point 905 based on information about the position of the target point 904 and data on the shape of the surface 901 of the breast and outputs the position to a body-surface-point mark generation unit 116. The 3D body mark generation unit 114 generates a 3D body mark based on the data on the shape of the surface 901 of the breast. FIG. 8 illustrates an example of the 3D body mark of the breast. The 3D body mark generation unit 114 outputs the generated 3D body mark 800 to the display control unit 120.

The body-surface-point mark generation unit 116 generates a body-surface-point mark 805 expressing the position of the body-surface point 905 on the 3D body mark 800 based on information about the position of the body-surface point 905 and outputs the body-surface-point mark 805 to the display control unit 120. The probe mark generation unit 118 calculates a probe mark 811 representing the position and orientation of the ultrasonic probe 611 on the 3D body mark 800 and outputs the probe mark 811 to the display control unit 120. The display control unit 120 causes the display unit 124 to display a position where an ultrasonic image acquired by the ultrasonic probe is captured and the position of the identified body-surface point 905 thereon. The display control unit 120 superimposes the position where the ultrasonic image is captured and the position of the identified body-surface point of the subject on at least either of the body mark image of the subject or the image acquired by capturing the subject to display. For example, the 3D body mark 800, the body-surface-point mark 805, and the probe mark 811 are combined with one another according to information about position. Furthermore, those are combined with the ultrasonic tomographic image 700 and displayed on the display unit 124.

At least one of each of the units of the information processing apparatus 100 illustrated in FIG. 1 may be realized as an independent apparatus. Alternatively, each of the units may be realized as a software to realize functions by installing the software in one or a plurality of computers and executing it by the central processing unit (CPU) of the computer. In the present exemplary embodiment, each unit is realized by software installed in the same computer.

Figure 2:
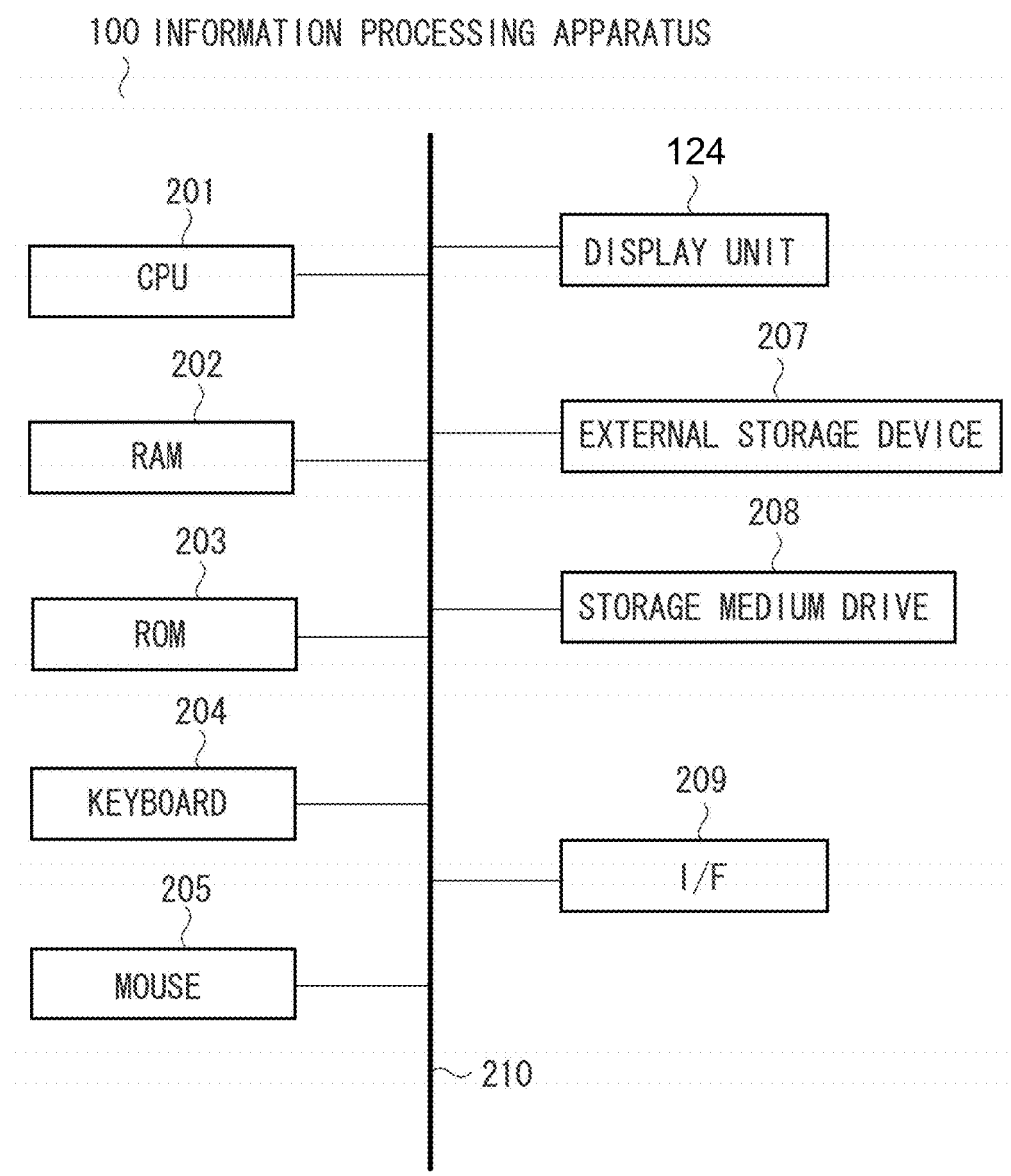
FIG. 2 illustrates the basic configuration of a computer capable of realizing each unit of the information processing apparatus by using software.

FIG. 2 illustrates the basic configuration of a computer for realizing the functions of each of the units in FIG. 1 by executing software. A CPU 201 controls the entire computer using programs and data stored in a random access memory (RAM) 202 and a read-only memory (ROM) 203. The CPU 201 controls the execution of software in each of the units to realize the function of each of the units. The RAM 202 includes an area for temporarily storing programs or data loaded from an external storage device 207 or a storage medium drive 208 and a work area required for the CPU 201 performing various types of processes as well.

In general, the ROM 203 stores computer programs and setting data. A keyboard 204 and a mouse 205 are input devices. An operator can input various instructions to the CPU 201 using the input devices. The program is the one that realizes the process illustrated in FIG. 3. A display unit 124 includes a cathode ray tube (CRT) or a liquid crystal display and displays the 3D body mark 800 or the ultrasonic tomographic image 700. Further, the display unit 124 can display a message to be displayed or a graphical user interface (GUI). The external storage device 207 functions as a mass information storage system such as a hard disk drive and stores programs executed by an operating system (OS) and the CPU 201. Information described as already known in the present exemplary embodiment is stored therein and loaded onto the RAM 202 if required.

The storage medium drive 208 reads the programs and data stored in a storage medium such as a compact disk (CD) ROM or a digital versatile disc (DVD) ROM according to instructions from the CPU 201 and outputs the programs and data to the RAM 202 and the external storage device 207. An interface (I/F) 209 includes an analog video port or digital input output port such as the Institute of Electrical and Electronics Engineers 1394 (IEEE1394) and an Ethernet port for outputting various pieces of information to the outside. The input data are stored in the RAM 202 via the I/F 209. A portion of the functions of the three dimensional medical image acquisition unit 102, the target-point position specifying unit 104, the tomographic image acquisition unit 106, the position and orientation acquisition unit 108, and the probe mark generation unit 118 is realized by the I/F 209. The components described above are connected with one another via a bus 210.

Figure 3:
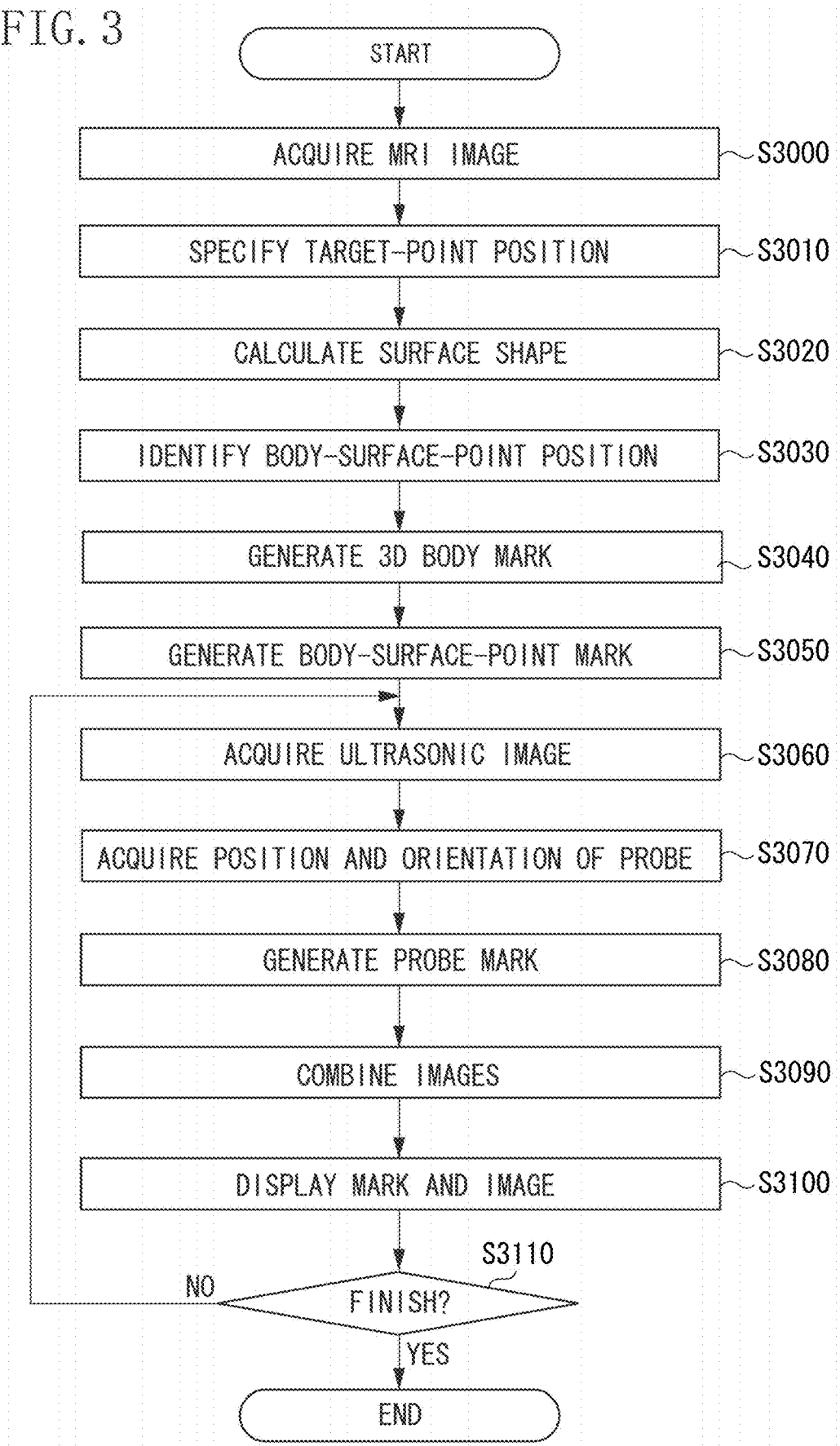
FIG. 3 is a flow chart illustrating the whole processes in the first exemplary embodiment.

FIG. 3 is a flow chart illustrating the process of an information processing method for supporting capture by the ultrasonic probe 611. In the present exemplary embodiment, the flow chart is realized by the CPU 201 executing the programs for realizing the functions of each of the units. Program codes in compliance with the flow chart are presumed to be loaded on the RAM 202 from the external storage device 207, for example, in a preceding stage where the following process is performed.

In step S3000, the three dimensional medical image acquisition unit 102 acquires the MRI image 900 of the breast in the supine position which is input from the data server 190 to the information processing apparatus 100.

In step S3010, the target-point position specifying unit 104 specifies the target point 904 (the center of the lesion area 903) based on information about position which is input from the data server 190 to the information processing apparatus 100.

In step S3020, the surface shape calculation unit 110 extracts shape data on the surface 901 of the breast from the MRI image 900. In the present exemplary embodiment, the MRI image 900 is binarized by an appropriate threshold to acquire a label image indicating a body area including a breast area. The shape of the surface 901 of the breast is represented by a position-coordinate vector group of voxels at an interface where the voxel value of the label image is switched.

In step S3030, the body-surface-point position identifying unit 112 identifies the position of body surface of the subject based on the position of the target point 904 inside the subject. The position of the body-surface point 905 which is extended from the target point 904 of the MRI image 900 to the surface 901 of the breast is calculated to identify the position of the body-surface point 905. In the present exemplary embodiment, the distance is calculated from each position forming a position-coordinate vector group representing the shape of surface 901 of the breast to the position of the target point 904. The position which is the smallest in distance is selected. The selected position is taken as the position of the body-surface point 905.

In step S3040, the 3D body mark generation unit 114 generates the 3D body mark 800 based on the shape data of the surface 901 of the breast. Specifically, the 3D body mark generation unit 114 generates the 3D body mark 800 based on the position-coordinate vector group (point group) representing the shape of the surface 901 of the breast. A triangular mesh is generated by a method for generating a mesh using a known Poisson's equation discussed in a literature, for example, M. Kazhdan, M. Bolitho, H. Hoppe, "Poisson Surface Reconstruction." Proc. Symposium on Geometry Processin, pp. 61-70, 2006.

In step S3050, the body-surface-point mark generation unit 116 generates the body-surface-point mark 805 at the position of the body-surface point 905. For example, the body-surface-point mark generation unit 116 generates a 5 mm in radius mesh ball at the position of the body-surface point 905 and uses the mesh ball as the body-surface-point mark 805.

In step S3060, the tomographic image acquisition unit 106 acquires the ultrasonic tomographic image 700 sequentially input from the second image capturing apparatus 182 to the information processing apparatus 100.

In step S3070, the position and orientation acquisition unit 108 acquires the position and orientation of the ultrasonic probe 611 in the sensor coordinate system 620 sequentially input from the position and orientation measuring apparatus 184 to the information processing apparatus 100.

(In step S3080, the probe mark generation unit 118 generates the probe mark 811 according to the position and orientation of the ultrasonic probe 611. For example, based on the position and orientation of the ultrasonic probe 611 acquired in step S3070, the probe mark generation unit 118 converts the position and orientation of a previously generated rectangular solid body, which approximately indicates the shape of the ultrasonic probe 611, and uses it as the probe mark 811.

In step S3090, the display control unit 120 combines, on the 3D body mark 800, the body-surface-point mark 805 with the probe mark 811.

In step S3100, the display control unit 120 causes the display unit 124 to display a position where an ultrasonic image acquired by the ultrasonic probe 611 is captured and the position of the identified body-surface point 905 thereon. The display control unit 120 causes the display unit 124 to display the image combined in step S3090. The 3D body mark 800 is superimposed at a predetermined position on the ultrasonic tomographic image 700 acquired in step S3060 and displayed. The display of the mark and the image is dynamically changed by the display control unit 120 according to the change of position of the ultrasonic probe 611.

In step S3110, the information processing apparatus 100 determines whether to end the entire process. For example, the operator clicks an end button arranged on the display unit 124 with the mouse 205 to input the determination of end. If the CPU 201 determines that the entire process is to be ended (YES in step S3110), the entire process of the information processing apparatus 100 is ended. If the CPU 201 determines that the entire process is not to be ended (NO in step S3110), the process is returned to step S3060 to subject again the newly acquired position and orientation data of the ultrasonic tomographic image 700 and the ultrasonic probe 611 to the processes from step S3060 to S3100. Although the present exemplary embodiment describes a case, as an example, where a breast of a human body is taken as a subject, the present exemplary embodiment of the present invention is not limited to the breast but any subject may be taken as a subject. Furthermore, although the present exemplary embodiment describes an example in which the center of a lesion area indicated in an MRI image is taken as a target point, the target point in the embodiments of the present invention is not limited to the center of a lesion area, but the center of an area indicating a treatment scar such as biopsy in an MRI image or the center of an area indicating hematoma may be taken as a target point. Furthermore there may be a plurality of target points.

As described above, the information processing apparatus 100 according to the present exemplary embodiment acquires the shape of surface of an object from the image of the object captured by a first medical imaging diagnostic apparatus, acquires the position and orientation of a probe in capturing the subject by a second medical imaging diagnostic apparatus, and acquires the position of a target point in the image. The information processing apparatus 100 calculates the position of the body-surface point extended from the target point to the surface and displays information about the position of the body-surface point and the position of the probe. This allows providing a mechanism for displaying information about the position of the body-surface point extended from the target point in the subject to the surface of the subject together with information about the position of the ultrasonic probe. Consequently, the operation of the ultrasonic probe can be supported while referring to information about the position of the body-surface point and the ultrasonic probe. For example, the position of the body-surface point extended from the target point in the MRI image of the breast in the supine position to the surface of the breast is calculated to allow displaying, on the 3D body mark indicating the breast in the supine position, the body-surface-point mark indicating the position together with the probe mark. For this reason, the operation of the ultrasonic probe can be supported while referring to information about the position of the body-surface point and the ultrasonic probe.

A modification will be described below. The present exemplary embodiment describes above the case where the body-surface-point mark 805 is displayed on the position of the body-surface point on the 3D body mark 800 as an example of process of the display control unit 120 in step S3090, however, the present exemplary embodiment of the present invention is not limited to that, for example, information about a distance between the body-surface point and the target point may be displayed without displaying the body-surface-point mark 805 on the position of the body-surface point. Alternatively, information about the distance between the body-surface point and the target point may be superimposed on the body-surface-point mark 805 to be displayed.

A case where the position of the body-surface point is not limited to the position of surface of the subject most adjacent to the target point is described below as another modification. The present exemplary embodiment describes the case where the point smallest in distance between the target point 904 and the surface 901 of the breast is taken as the body-surface point 905 as an example of process of the body-surface-point position identifying unit 112 in step S3030, however, the present exemplary embodiment of the present invention is not limited to that, for example, the intersection of a segment extending from the target point 904 to the Y axis direction (gravity axis direction) of the MRI coordinate system and the surface 901 of the breast may be taken as the position of the body-surface point 905. In this case, the position of the ultrasonic probe 611 is caused to agree with the position of the body-surface point 905 and the orientation of the ultrasonic probe 611 is caused to agree with an axial cross section or a sagittal cross section, which means that a lesion area 703 is included in a plane represented by the ultrasonic tomographic image 700.

Alternatively, the intersection of a segment extending from the target point 904 to the X axis direction of the MRI coordinate system and the surface 901 of the breast may be taken as the position of the body-surface point 905. In this case, the position of the ultrasonic probe 611 is caused to agree with the position of the body-surface point 905 and the orientation of the ultrasonic probe 611 is caused to agree with the axial cross section or a coronal cross section, which means that the lesion area 703 is included in the plane represented by the ultrasonic tomographic image 700. Similarly, the intersection in the Z axis direction in the MRI coordinate system is taken as the position of the body-surface point 905 and the orientation of the ultrasonic probe 611 is caused to agree with the coronal cross section or the sagittal cross section, which means that the lesion area 703 is included in the plane represented by the ultrasonic tomographic image 700.

A normal is calculated at each position which forms a position-coordinate vector group representing the surface 901 of the breast, and then a distance to the target point 904 is acquired from each calculated normal, and a position where the distance is smaller than a predetermined distance may be taken as the position of the body surface point 905. If a plurality of candidate positions is acquired, for example, the candidate position that is the nearest to the position of the target point 904 may be selected as the position of the body surface point 905.

As a modification, a case will be described below in which the position of the body surface point 905 is displaced because the probe cannot be placed on the position of the body surface point 905. The present exemplary embodiment describes a case, as an example, in which a position where a distance between the target point 904 and the surface 901 of the breast is minimal is taken as the position of the body surface point 905. However, if the position of the body surface point 905 approximately agrees with the position of a nipple 902, for example, it is difficult to acquire an appropriate ultrasonic image such that the position of the ultrasonic probe 611 is caused to agree with the position of the body-surface point 905. In the present modification, the body-surface-point position identifying unit 112 acquires information, which is stored correspondingly with at least any of an imaging portion and information about a patient, about the predetermined area of the subject. Thereafter, the body-surface-point position identifying unit 112 identifies the position of the body surface so that the position of the body surface of the subject identified by the body-surface-point position identifying unit 112 is not identified in the predetermined area.

The following describes an example of process. The body-surface-point position identifying unit 112 determines whether the position of the nipple 902 inadequate for ultrasonic imaging substantially agrees with the position of the body-surface point 905. If the position of the nipple 902 substantially agrees with that of the body-surface point 905, the position of the body-surface point 905 is displaced by a predetermined distance (10 mm, for example) in the direction of the probe mark, for example. As an example of another process, the body-surface-point position identifying unit 112 removes the aforementioned predetermined area from the range of the body surface identified as the body-surface point 905 and identifies the shortest path from the range to be left after removal. The term predetermined area being a removal area refers to a nipple if the breast, for example, is imaged as an imaging portion, however, an area which includes the nipple and is sufficiently larger than the nipple area may be taken as the removal area in consideration of the size of an ultrasonic probe and a burden to a subject.

At this point, the moved body-surface-point mark is displayed in a mode (with color and shape changed) different from a general body-surface-point mark to allow displaying a guide explicitly indicating that a portion to be avoided exists. In addition, the body-surface-point marks before and after movement may be displayed at the same time.

Other embodiments excluding MRI will be described below as modifications. In the present exemplary embodiment, the MRI apparatus is used as the first image capturing apparatus 180 and the MRI image acquired by the MRI apparatus is described as an example, however, the present exemplary embodiment of the present invention is not limited to that. For example, an X-ray CT apparatus for capturing a CT image, a photoacoustic tomography apparatus, an OCT apparatus, a PET/SPECT, and a three dimensional ultrasonic apparatus may be used.

Figure 4:
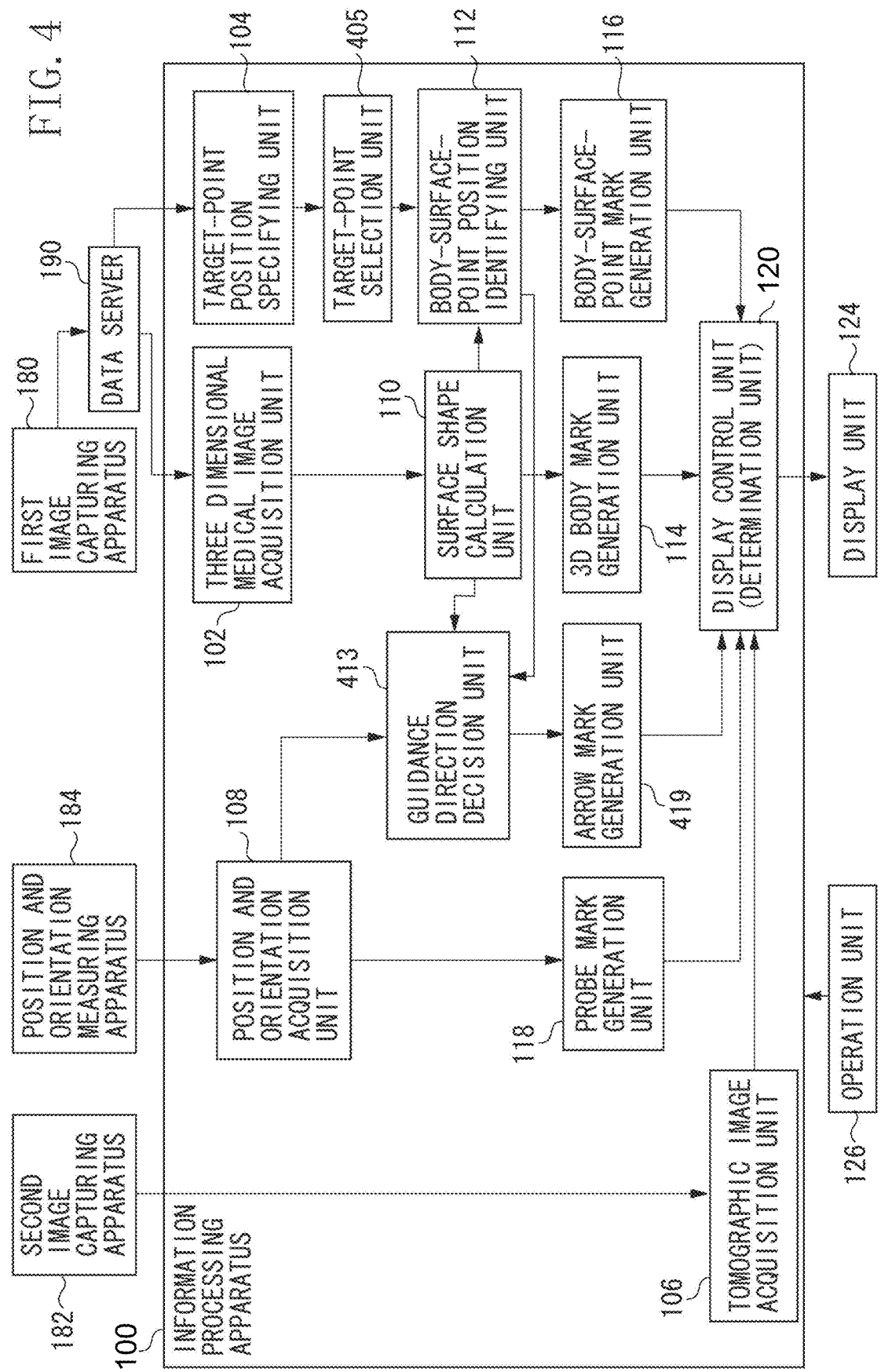
FIG. 4 illustrates a device configuration of an information processing apparatus according to a second exemplary embodiment.

The present exemplary embodiment describes below a case in which information about direction in which an ultrasonic probe is to be moved along the surface of a subject is also displayed on a 3D body mark, in addition to the process of the foregoing exemplary embodiments. FIG. 4 illustrates a configuration of an information processing apparatus 100 according to the present exemplary embodiment. The components similar to those in FIG. 1 are given the same reference numerals and symbols, so that the description thereof is omitted herein.

If there is a plurality of target points 904, a target-point selection unit 405 acquires information about selection of the target points to which a probe is guided and outputs information about the position of the selected target point 904 to the body-surface-point position identifying unit 112. A guidance direction decision unit 413 decides the direction in which the ultrasonic probe 611 is to be moved along the body surface based on the capture position of the ultrasonic probe 611 measured by the position and orientation measuring apparatus 184 and the body-surface point 905. The guidance direction decision unit 413 calculates, based on, for example, the position and orientation of the ultrasonic probe 611 and the position information of the target point 904 and data on the shape of the surface 901 of the breast, a three dimensional vector representing the direction in which the ultrasonic probe 611 is guided. The guidance direction decision unit 413 outputs the three dimensional vector to an arrow mark generation unit 419 to urge the user to change the capture position of the ultrasonic probe 611 to the specified position along the direction.

Figure 10:
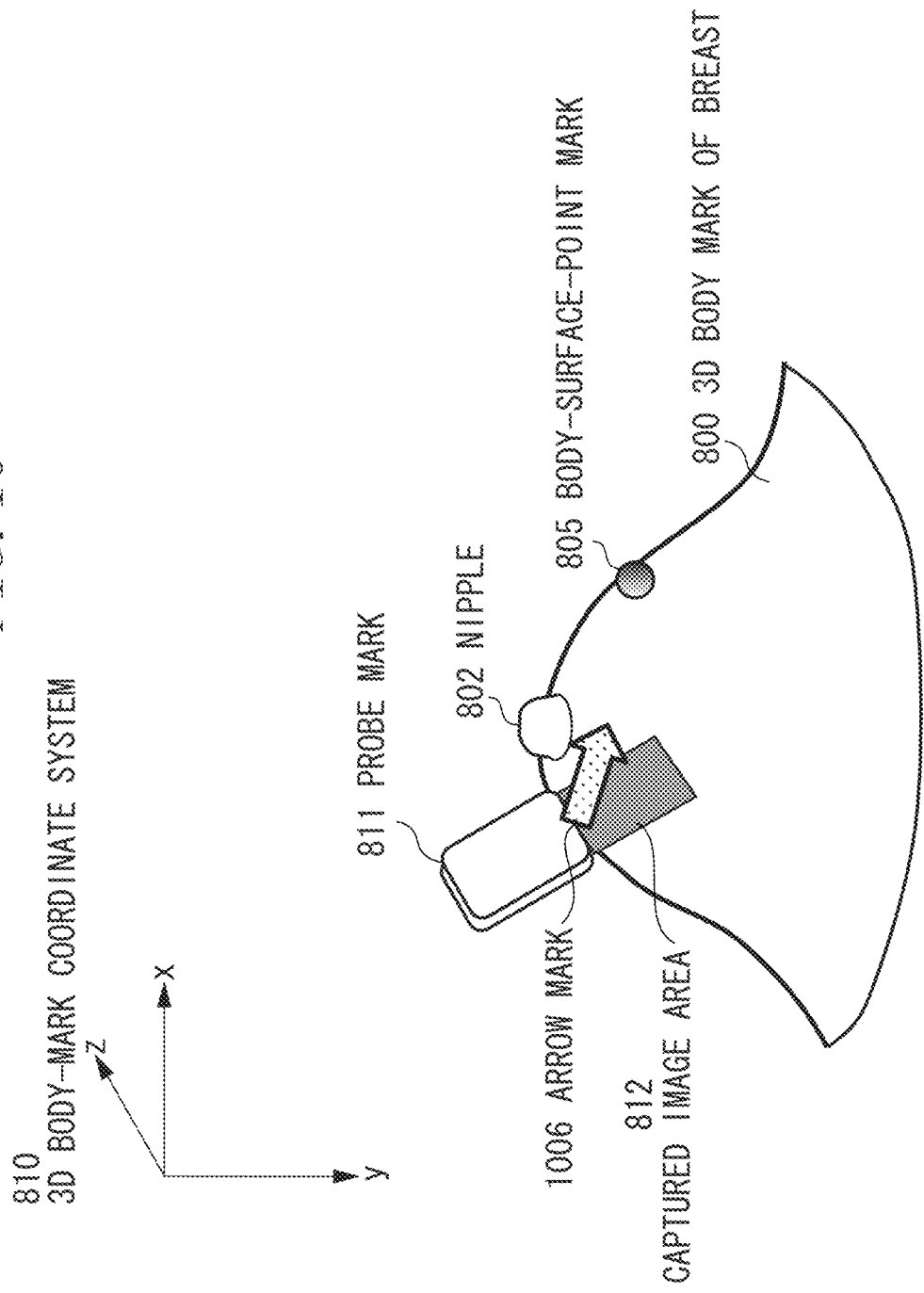
FIG. 10 illustrates an example of an arrow mark on the 3D body mark.

The arrow mark generation unit 419 generates an arrow mark based on the three dimensional vector representing the direction in which the ultrasonic probe 611 is guided. FIG. 10 illustrates a display example of the arrow mark. The portions similar to those in FIG. 8 are given the same reference numerals and symbols. The arrow mark generation unit 419 outputs the generated arrow mark 1006 to a display control unit 120. The display control unit 120 combines the 3D body mark 800, the body-surface-point mark 805, the probe mark 811, and the arrow mark 1006 with one another. The display control unit 120 further combines the ultrasonic tomographic image 700 with those marks and displays the combination on the display unit 124.

Figure 5:
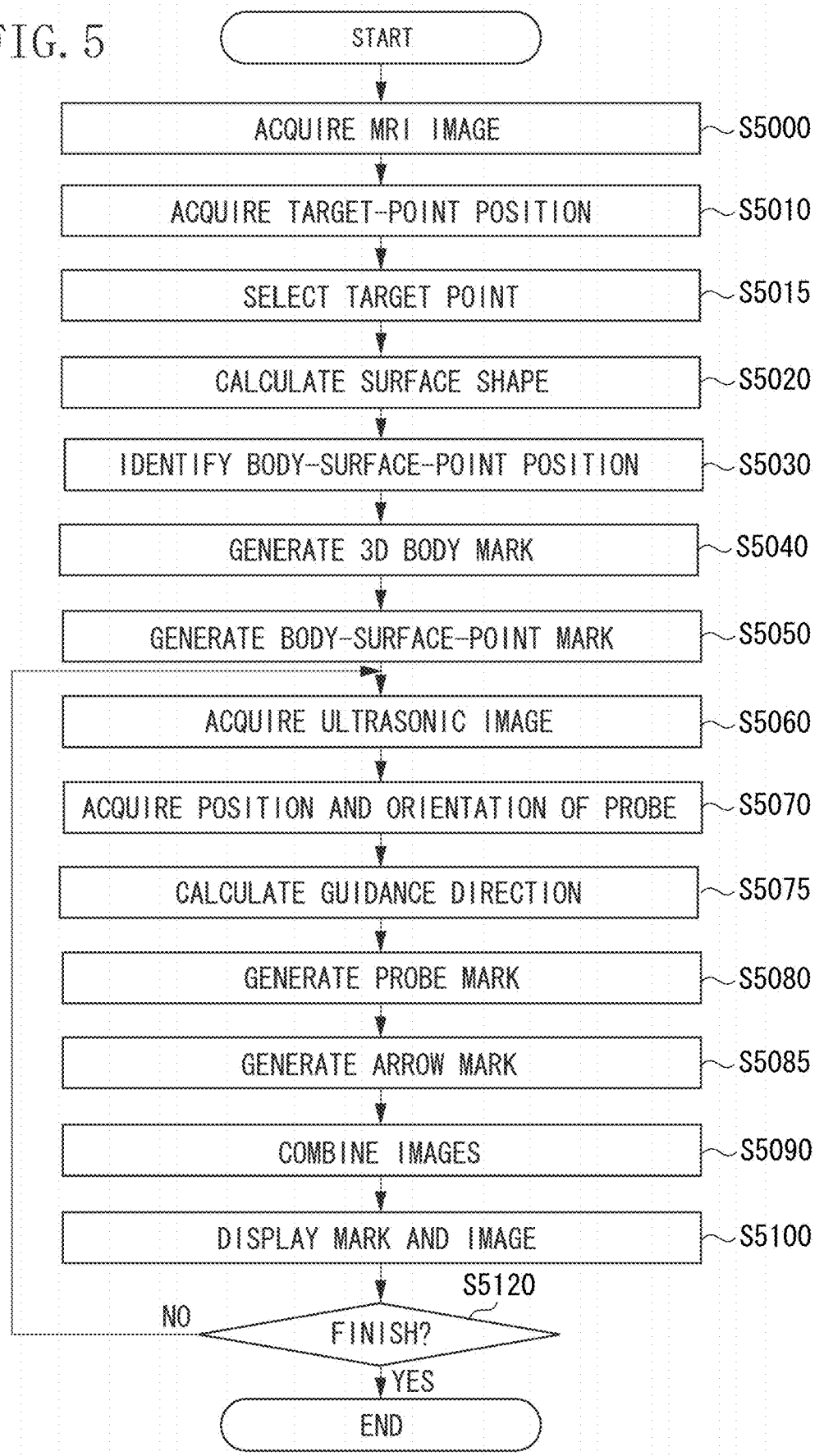
FIG. 5 is a flow chart illustrating the processes in the second exemplary embodiment.

FIG. 5 is a flowchart illustrating the entire process of the information processing apparatus 100 shown in FIG. 4. The flowchart is different from that of the foregoing exemplary embodiment in that the processes of steps S5015, S5075, and S5085 are added and the process of step S5090 is performed instead of the process of step S3090. The following describes the process of only each of above steps. The flow chart is realized by the CPU 201 executing programs for realizing the function of each unit. Before the following processes are performed, the program codes according to the flow chart are already loaded to the RAM 202 from the external storage device 207, for example.

In step S5015, if there is a plurality of target points 904, the target-point selection unit 405 acquires information about selection of the target points to which the probe is guided. For example, the operator clicks selection buttons, the number of which is equal to that of the target points, arranged on the display unit 124 with the mouse to input information about selection of the target point.

In step S5075, the guidance direction decision unit 413 calculates the three dimensional vector representing the direction along the surface 901 of the breast for guiding the ultrasonic probe 611. More specifically, the guidance direction decision unit 413 calculates the three dimensional vector Vcs from the position Xc of a central portion 612 of leading edge of the ultrasonic probe in an MRI coordinate system 910 to the position Xs of the body-surface point 905. Furthermore, the guidance direction decision unit 413 calculates the three dimensional vector Vcs' representing the direction along the surface 901 of the breast such that the vector Vcs is rotated around the X axis of a probe coordinate system 610 so that an angle made by a normal vector Vc on the surface 901 of the breast in the position Xc and the vector Vcs becomes 90 degrees.

In step S5085, the arrow mark generation unit 419 generates the arrow mark 1006 based on the three dimensional vector Vcs' representing the direction in which the ultrasonic probe 611 is guided. For example, the position and orientation of a three directional arrow model previously generated are converted according to the direction of the vector Vcs' and used as the arrow mark 1006.

In step S5090, the display control unit 120 combines, on the 3D body mark 800, the body-surface-point mark 805, the probe mark 811, and the arrow mark 1006 with one another. The display control unit 120 superimposes the 3D body mark 800 onto a predetermined position on the ultrasonic tomographic image 700 acquired in step S5060.

In step S5100, the display control unit 120 causes the display unit 124 to display the image combined in the above process. The display of the mark and the image is dynamically changed according to the change of position of the ultrasonic probe. As described above, in the present exemplary embodiment, the guidance direction decision unit 413 decides the direction in which the probe needs to be moved based on the position of the body-surface point and the probe. The display control unit 120 causes the display unit 124 to display the decided direction along with the capture position and the specified position in the body surface. This allows providing a mechanism for displaying the direction in which the ultrasonic probe needs to be moved along the surface of the subject. For this reason, it is possible to support the operation of the ultrasonic probe with reference to information about the position of the body-surface point and the ultrasonic probe and information about the direction in which the ultrasonic probe needs to be moved.

For example, there can be provided a mechanism for displaying, on the 3D body mark, information about the direction in which the ultrasonic probe needs to be moved along the surface of the subject. For this reason, it is possible to support the operation of the ultrasonic probe with reference to information about the position of the body-surface point and the ultrasonic probe and information about the direction in which the ultrasonic probe needs to be moved. Furthermore, in the present exemplary embodiment, the display unit 124 displays the direction in which the ultrasonic probe is moved along the body surface while sequentially displaying the ultrasonic image captured at a predetermined frame rate. This allows the user to be provided with the direction in which the probe is moved with the ultrasonic probe kept in contact with the body surface and the tomographic image of the subject kept being captured. The user can appropriately move the ultrasonic probe while confirming the direction and continuously observing the image of the subject to produce an effect that the user can more easily observe the subject.

A case is described below, as a modification, in which a nipple is detoured. The present exemplary embodiment describes the case in which the vector representing the direction in which the ultrasonic probe is guided is calculated based on the position and orientation of the ultrasonic probe 611 and the position information of the target point 904 and data on the shape of the surface 901 of the breast as an example of the process of the guidance direction decision unit 413 in step S5075. However, if the nipple 902, for example, exists on a straight line extended from the position of the ultrasonic probe 611 to the direction of the vector, it is difficult to acquire an appropriate ultrasonic image while operating the ultrasonic probe 611 along the vector. In the present modification, therefore, a determination is made as to whether a distance between the position of the nipple 902 inadequate for ultrasonic imaging and the abovementioned straight line is shorter than a predetermined distance (20 mm, for example), if the distance is shorter than the predetermined distance, the three dimensional vector is recalculated. More specifically, such a way-stop that the distance between the position of the nipple 902 inadequate for ultrasonic imaging and the position of the ultrasonic probe 611 always becomes greater than the predetermined distance is set on the surface 901 of the breast and the three directional vector toward the way-stop is recalculated.

In the present modification described above, a nipple area in the breast is taken as an example. Aside from the nipple area, an imaging portion such as the breast and the abdominal region and a predetermined exclusion area (predetermined area) corresponding to information about a patient such as sexuality are made ready to be set and stored in a storage unit (not illustrated) in the information processing apparatus or the data server 190. The guidance direction decision unit 413 acquires information about such an exclusion area to decide the direction in which the ultrasonic probe 611 is moved to detour the exclusion area (predetermined area). Thereby, even if the predetermined area where the ultrasonic probe should not be placed on the body surface exists, it is possible to properly instruct the user to follow the direction in which the ultrasonic probe is moved along the body surface.

Finally, a case is described below, as a second modification, in which the probe is rotated at the body-surface position (a guide display for changing only orientation so that the probe is provided with a proper orientation). The present exemplary embodiment describes above the case, as an example, in which information about the direction in which the ultrasonic probe 611 needs to be moved along the surface of the subject is displayed on the 3D body mark. The present modification is not limited to this example, but causes the display unit 124 to display instructions for changing the orientation of the ultrasonic probe 611 to properly capture the specified target point 904.

In this case, the body-surface-point position identifying unit 112 also specifies the orientation of the ultrasonic probe 611 so that the position of the specified target point 904 falls within a captured image range 712 of the ultrasonic probe 611. The guidance direction decision unit 413 decides the direction in which the ultrasonic probe 611 needs to be moved to change the orientation of the ultrasonic probe 611 to the specified orientation. The direction in which the ultrasonic probe 611 needs to be rotated is calculated so that a distance between a plane representing a captured image area 812 and the target point 904 is decreased. The arrow graphic, which represents the direction that needs to be rotated and is displayed by the display control unit 120, is displayed in a mode (in a different color or shape) different from the arrow graphic representing the direction in which the ultrasonic probe 611 is guided to the body surface point 905. This performs the guide display of not only the position of the body surface on which the ultrasonic probe 611 needs to be placed, but also the orientation of the ultrasonic probe 611 relative to the body surface, which allows a further improvement in user convenience.

In addition to that, an arrow graphic is also displayed which represents the direction in which the ultrasonic probe 611 needs to be moved to get an appropriate orientation after the ultrasonic probe 611 reaches the vicinity of the body-surface position. In this case, the display control unit 120 functions as a determination unit which determines whether the distance between the measured capture position of the ultrasonic probe 611 and the specified position of the body surface point 905 becomes equal to or smaller than a predetermined threshold. The display control unit 120 causes the display unit 124 to display the direction in which the ultrasonic probe 611 is moved to change the orientation according to the results of the determination. If the distance between the ultrasonic probe 611 and the body surface point 905 is greater than the predetermined threshold, the display control unit 120 does not cause the display unit 124 to display instructions for the direction about the orientation. If the distance between the ultrasonic probe 611 and the body surface point 905 is equal to or smaller than the predetermined threshold, the display control unit 120 causes the display unit 124 to display instructions for the direction about the orientation. This eliminates issuing at the same time a plurality of instructions related to the position and orientation to the user to improve the user's understanding of the display and convenience. If the guidance direction decision unit 413 decides the direction which the ultrasonic probe 611 needs to be rotated to get an appropriate orientation for the first time after the ultrasonic probe 611 reaches the vicinity of the body-surface position, the burden of process for determining a guidance direction about the orientation can be reduced.

Figure 11:
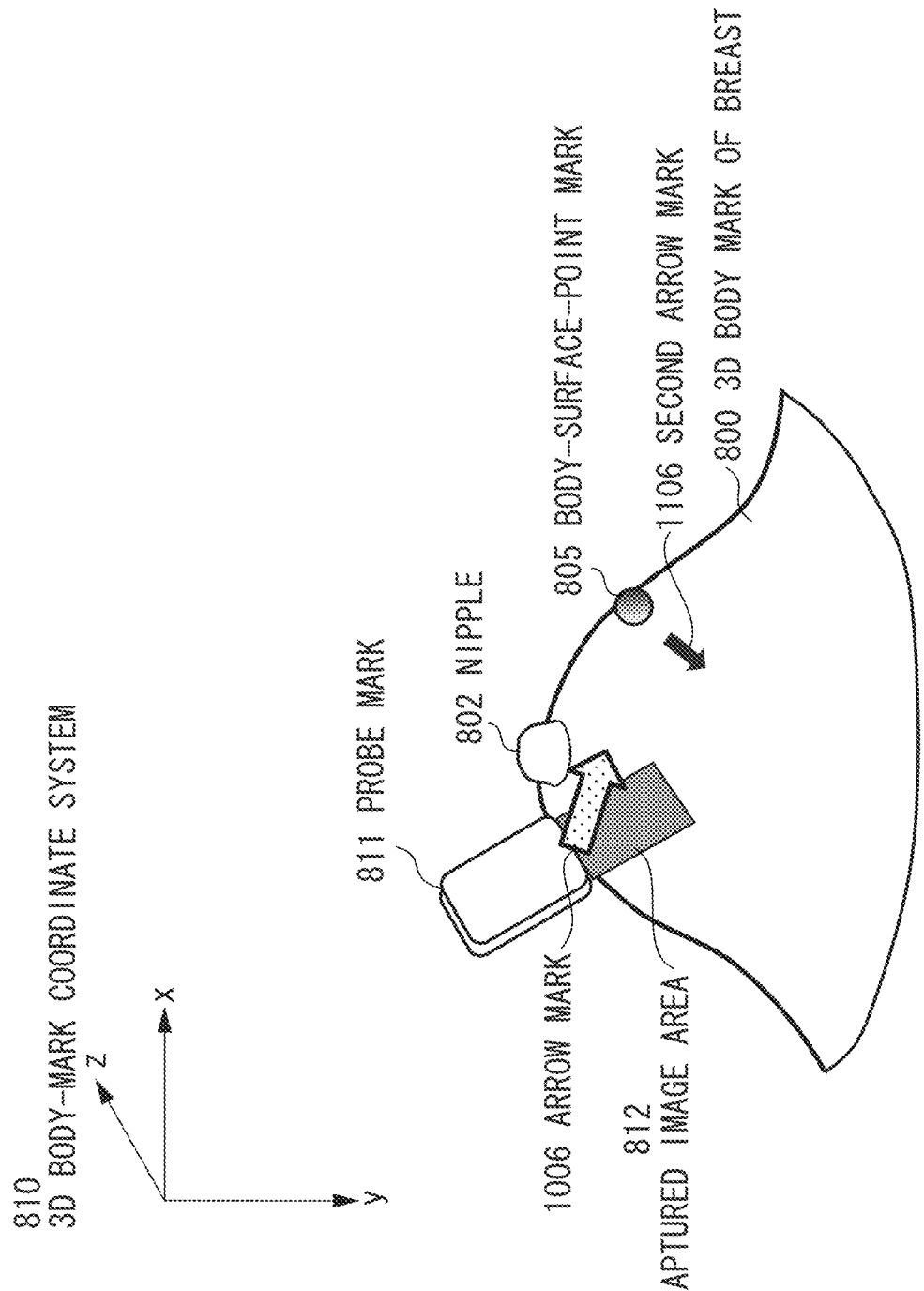
FIG. 11 illustrates another display example of the arrow mark on the 3D body mark.

A third modification will be described below. As illustrated in FIG. 11, the display control unit 120 causes the display unit 124 to display a second arrow mark 1106 representing the direction from the body-surface point 905 to the target point 904 as well as the arrow mark (a first arrow mark 1006). The direction of the second arrow mark 1106 is calculated and obtained by the guidance direction decision unit 413. The guidance direction decision unit 413 calculates and obtains the direction from the body-surface point 905 to the target point 904 based on a relationship between the positions of the target point 904 and the body-surface point 905. The guidance direction decision unit 413 decides the obtained direction as the direction to which the imaging plane of the ultrasonic probe 611 needs to be oriented. The display control unit 120 superimposes the probe mark 811 representing the capture position of the ultrasonic probe 611, the body-surface-point mark 805 expressing the position of the body-surface point 905, the first arrow mark 1006, and the second arrow mark 1106 on the 3D body mark 800 and displays the superimposed marks. Objects on which the marks are superimposed may be a three dimensional MRI image or a CT image. If the marks are superimposed on a two dimensional body mark or an MRI image, the direction determined by the guidance direction decision unit 413 is projected on the plane of the body mark or the cross section of the MRI image, and the projected direction may be calculated and displayed.

Thereby, the user can easily grasp the target position of the ultrasonic probe 611, a method for moving the probe to the target position, and the direction to which the imaging plane is oriented, from the display screen. The body-surface-point position in the above exemplary embodiment is a point (a quiescent point) uniquely determined from the target point and the shape of the body surface. Instead of this, in the present exemplary embodiment, the position of the body-surface point suited for the current orientation of the ultrasonic probe 611 is dynamically determined based on the position of the specified target point 904 and the orientation of the ultrasonic probe 611 measured by the position and orientation measuring apparatus 184 and displayed on the display unit 124. The following describes only the points of the information processing apparatus according to the present exemplary embodiment which are different from those of the information processing apparatus according to the above exemplary embodiment.

An information processing apparatus according to the present exemplary embodiment is similar in configuration to the one illustrated in FIG. 1. However, the information processing apparatus according to the present exemplary embodiment is different therefrom in that the orientation of the ultrasonic probe 611 acquired by the position and orientation acquisition unit 108 is input to the body-surface-point position identifying unit 112 and the body-surface-point position identifying unit 112 uses the orientation of the ultrasonic probe 611 in calculating the position of the body-surface point. The body-surface-point position identifying unit 112 identifies the position of the body-surface point 905 as a target contact position between the ultrasonic probe 611 and the body surface. At this point, the body-surface-point position identifying unit 112 identifies the position of the body-surface point 905 so that the position of the specified target point 904 falls within the imaging range of the ultrasonic probe 611 with the orientation of the ultrasonic probe 611 measured by the position and orientation measuring apparatus 184 kept maintained.

A flow chart illustrating the entire process of the information processing apparatus according to the present exemplary embodiment is similar to the one in FIG. 3. However, the flow chart is different from the one in FIG. 3 in that the processes in steps S3030 and S3050 are not executed but the following processes of steps S3073 and S3077 are executed between steps S3070 and S3080. In step S3073, the body-surface-point position identifying unit 112 uses the orientation of the ultrasonic probe 611 acquired in step S3070 to calculate the body-surface position suited for the orientation of the current ultrasonic probe. The body-surface-point position identifying unit 112 calculates a −Y axis direction of the probe coordinate system 610 based on information about the orientation of the ultrasonic probe 611. The body-surface-point position identifying unit 112 determines a straight line extending from the position of the target point 904 along the −Y axis of the probe coordinate system 610. The body-surface-point position identifying unit 112 takes the intersection between the straight line and the surface 901 of the breast as the body-surface point 905. In step S3077, as is the case with step S3050 in the above exemplary embodiment, the body-surface-point mark generation unit 116 generates the body-surface-point mark 805 at the position of the body-surface point 905.

Thus, in the present exemplary embodiment, the position of the body-surface point extended from the target point to the surface is calculated based on the orientation of the ultrasonic probe. Thereby, the position of the body-surface point for which the ultrasonic probe needs heading according to the orientation of the current ultrasonic probe is changed to produce a further effect that a target point is easily visualized in a captured image when the ultrasonic probe reaches the displayed position of the body-surface point.

The body-surface-point position in the above exemplary embodiment is a uniquely determined point. In the third exemplary embodiment, the body-surface-point position suited for the orientation of the current ultrasonic probe 611 is dynamically determined. In the present exemplary embodiment, on the other hand, the position of the body-surface point 905 is dynamically selected from a plurality of candidate positions according to the position of the current ultrasonic probe 611 and displayed on the display unit 124. The following describes only the portions of the information processing apparatus according to the present exemplary embodiment which are different from those of the first to third exemplary embodiments.

Figure 12:
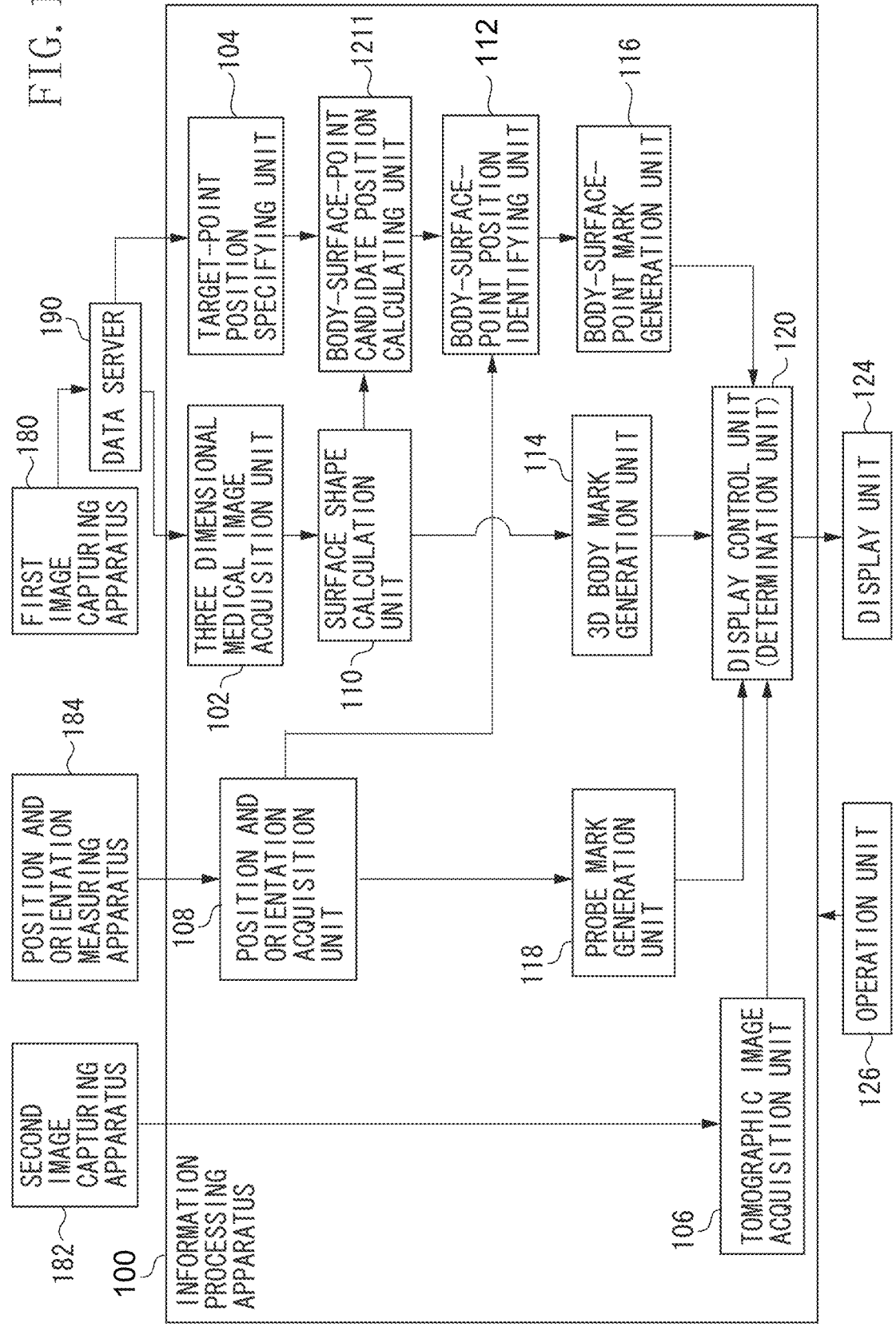
FIG. 12 illustrates a device configuration of an information processing apparatus according to a fourth exemplary embodiment.

FIG. 12 illustrates a configuration of an information processing apparatus 100 according to the present exemplary embodiment. The components similar to those in FIG. 1 are given the same reference numerals and characters, so that the description thereof is omitted herein. A body-surface-point candidate position calculating unit 1211 calculates the candidate position of a body-surface point 905 in the body surface of a subject based on the specified target point 904. The body-surface-point candidate position calculating unit 1211 calculates one or more candidate positions of the body-surface point 905 based on information about the position of the target point 904 and data on the shape of the surface 901 of the breast and outputs one or more candidate positions to a body-surface-point position identifying unit 112. The body-surface-point position identifying unit 112 identifies the position of the body-surface point 905 from among the candidate positions based on the position of the ultrasonic probe 611 acquired by the position and orientation acquisition unit 108.

Figure 13:
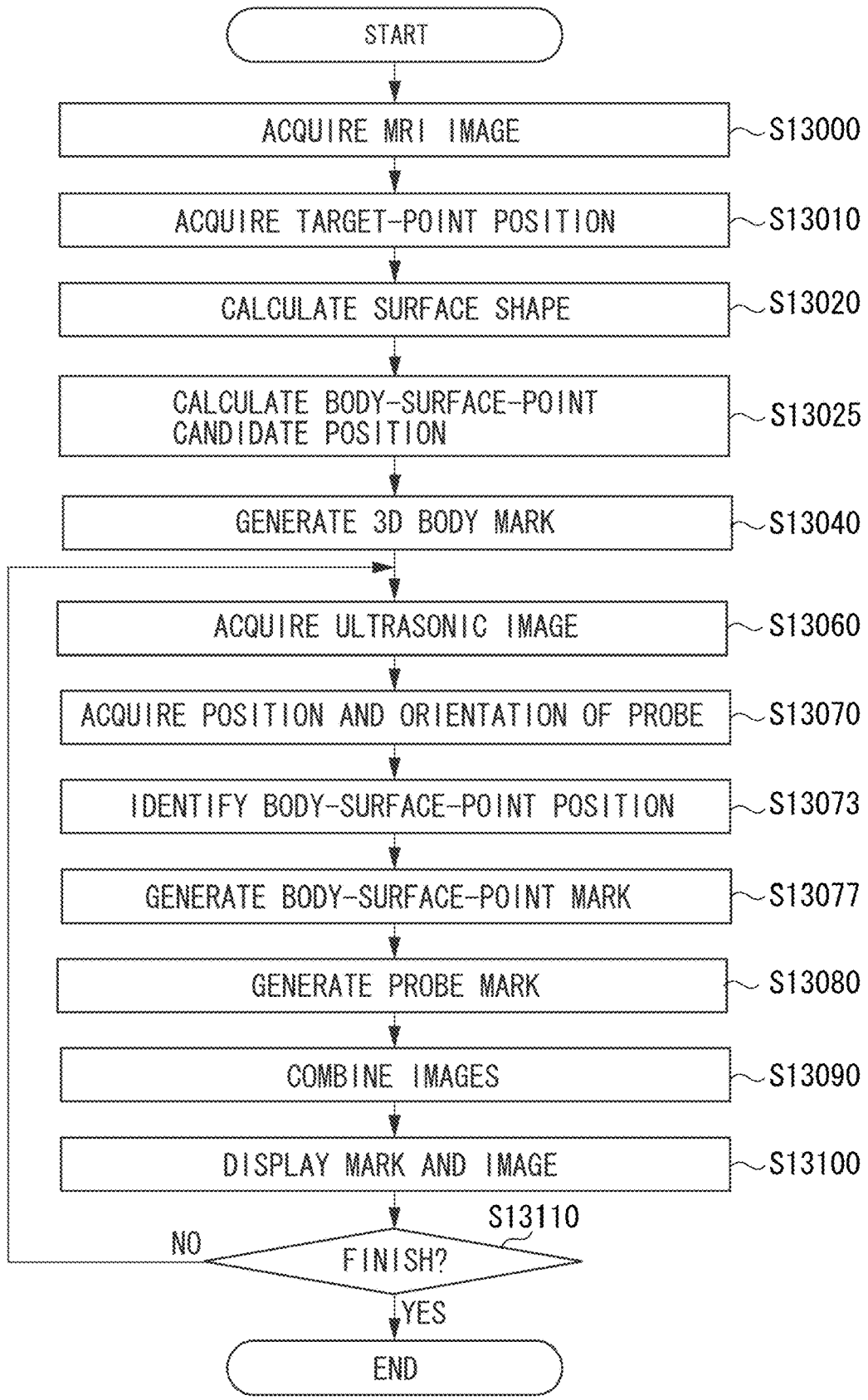
FIG. 13 is a flow chart illustrating the processes in the fourth exemplary embodiment.

FIG. 13 is a flow chart illustrating the entire process of the information processing apparatus 100 shown in FIG. 12. The flow chart is different from that of the first exemplary embodiment in that the processes corresponding to steps S3030 and S3050 are not executed. Furthermore, the flow chart is different therefrom in that the process in step S13025 is executed after the process corresponding to step S3020. Still furthermore, the flowchart is different therefrom in that the following processes in steps S13073 to 13077 are executed after the process corresponding to step S3070. The processes only in those steps are described below.

In step S13025, the body-surface-point candidate position calculating unit 1211 calculates a plurality of candidate positions as a candidate position of the body-surface point of a subject based on the position of the target point 904 inside the subject. In the present exemplary embodiment, the body-surface-point candidate position calculating unit 1211 calculates a normal at each position constituting a position-coordinate vector group representing the shape of surface 901 of the breast, determines a distance between each of the calculated normals and the target point 904, and takes the position where the distance becomes smaller than a predetermined distance as the candidate position of the body-surface point 905. More specifically, the body-surface-point candidate position calculating unit 1211 calculates a plurality of points, on a body surface, where the target point 904 lies in a substantially vertical direction viewed from the body surface as a probe position suited for capturing the target point 904 as a candidate position of the body-surface point 905. However, a point where a distance from the target point 904 is equal to or greater than the predetermined value (the imaging range of an ultrasonic wave in the depth direction, for example) is excluded from being the candidate. If the points, on the body surface, satisfying the condition are too close to each other (in other words, if a plurality of similar points is selected), only the point that is closer in distance from the target point 904 than any other points may be taken as a candidate position. Alternatively, points on the body surface may be selected in ascending order of distance from the target point 904 so that the number of candidate positions of the body-surface point 905 becomes equal to a predetermined number.

Regarding the description of the substantially vertical or normal direction, capturing is normally performed with the ultrasonic probe substantially vertically placed on the body surface, so that an exact vertical or normal direction is not required. An error of degree that the operator recognizes as the substantially normal direction, that is, at least plus or minus several degrees are allowed. In step S13073, the body-surface-point position identifying unit 112 uses the position of the ultrasonic probe 611 acquired in step S13070 to identify the body-surface position suited for the position of the current ultrasonic probe 611 from the candidate positions. Specifically, the body-surface-point position identifying unit 112 selects the candidate position closest in distance to the position of the ultrasonic probe 611 and takes the candidate position as the position of the body-surface point 905. A distance between the position of the ultrasonic probe 611 and the candidate position may be a geodetic-line distance along the body surface. Alternatively, the distance therebetween may simply be a straight-line distance between the two positions (Euclidean distance). Thereby, the operation time of the operator can be reduced and a proper image capturing can be realized.

Another exemplary embodiment is described below. The body-surface-point position identifying unit 112 takes a candidate position where an image can be captured without changing the tilt of the ultrasonic probe 611 as far as possible based on the orientation of the ultrasonic probe 611 as the position of the body-surface point 905. More specifically, each candidate position is stored associated with the orientation of the ultrasonic probe 611 for capturing the position of the target point 904. The body-surface-point position identifying unit 112 compares the orientation of the ultrasonic probe 611 with the stored orientation. As a result of the comparison, the candidate position which needs the least change of the orientation is identified and taken as the position of the body-surface point 905. Thereby, the change of orientation of the ultrasonic probe 611 can be reduced to allow facilitating the operation of the operator. In step S13077, as is the case with step S3050 in the first exemplary embodiment, a body-surface-point mark generating unit 1216 generates the body-surface-point mark 805 at the position of the body-surface point 905. At this point, a body-surface-point candidate mark may be generated in a display mode different from the one of the body-surface-point mark 805 at the candidate position calculated by the body-surface-point candidate position calculating unit 1211 as well as at the position of the body-surface point 905 identified by the body-surface-point position identifying unit 112. If a two dimensional body mark is used instead of the three dimensional body mark 800, a position where the position of the body-surface point 905 (and the candidate position) is projected on the plane of the body mark is calculated and the body-surface-point mark 805 (and the body-surface-point candidate mark) has only to be generated at the position.

Thus, in the present exemplary embodiment, the position of the body-surface point extended from the target point to the surface is calculated based on the position of the ultrasonic probe. This selects the position of the body-surface point closest to the position of the current ultrasonic probe to allow decreasing the workload of the user.

A first modification will be described below. The present exemplary embodiment describes above the case, as an example, in which the position of the body-surface point 905 is dynamically selected from a plurality of candidate positions according to the position of the current ultrasonic probe 611. The present modification is not limited to this, but the position of the body-surface point 905 is uniquely determined from a plurality of candidate positions based on the position of the ultrasonic probe 611 at a predetermined timing. The predetermined timing may be the timing at which the operator clicks a button arranged on the display unit 124 with the mouse 205, for example. Alternatively, the predetermined timing may be the timing at which the ultrasonic probe 611 comes into contact with the subject and the ultrasonic image inside the subject starts being acquired. The timing may be determined as to whether a difference between an ultrasonic image in a state where the ultrasonic probe 611 is not contact with the subject and the current ultrasonic image is equal to or greater than a certain value.

Another exemplary embodiment will be described below. In the above exemplary embodiments, the target point 904 and the body-surface point 905 are identified. Aside from those, a target area and a body-surface area based on the target area may be specified. In the above exemplary embodiments, the body-surface point 905 is identified as a point on the body surface. This is simply because the contact position where the ultrasonic probe captures an image while being contact with the body surface is clearly indicated and the body-surface point 905 has only to be identified not necessarily on the body surface, but on a position near the body surface.

In the above-described embodiments of the present invention, the above ultrasonic imaging system may be realized by dispersing the process by the plurality of equipments or the present embodiments may be applied to an apparatus formed of one equipment. The ultrasonic apparatus may be equipped with the ultrasonic probe 611, the position and orientation measuring apparatus 184, the display unit 124, and any of the information processing apparatuses in the above exemplary embodiments, for example.

The embodiments of the present invention includes a case in which a software program is directly or remotely supplied to a system or an apparatus and the computer of the system or the apparatus reads and executes the supplied program code to accomplish the functions of the above exemplary embodiments. In this case, the supplied program is a computer program corresponding to the flow chart illustrated in the graphic in the exemplary embodiments. Therefore, the program code itself installed into the computer to realize the function process of the embodiments of the present invention by the computer also realizes the embodiments of the present invention. In other words, the embodiments of the present invention includes the computer program itself for realizing the function process of the embodiments of the present invention. Not only the functions of the above exemplary embodiments are realized by executing the programs read by the computer, but also the functions of the exemplary embodiments may be realized in collaboration with the OS operated on the computer based on the instructions of the programs. In this case, the OS performs a part or all of actual processes to realize the functions of the above exemplary embodiments. Furthermore, a part or all of the functions of the above exemplary embodiments may be realized by writing the programs read from a recording medium in a memory included in a function extension board inserted into the computer or a function extension unit connected with the computer. In this case, the programs are written in the memory of the function extension board or the function extension unit and then the CPU in the function extension board or the function extension unit performs a part or all of actual processes based on the instructions of the programs.

According to the exemplary embodiments of the present invention, it is possible to display a position on a body surface based on the position specified in a three dimensional image and a position where an image is captured by an ultrasonic probe. Thereby, the user can easily confirm where the ultrasonic probe needs to be moved, from a display, only by specifying a position to be desired to be viewed on the three dimensional image.

The embodiment can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present disclosure has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. An image processing apparatus for supporting imaging performed by an ultrasonic probe that acquires an ultrasonic image of a subject, the image processing apparatus comprising:
   a memory storing a program; and
   one or more processors which, by executing the program, function as:
      an acquisition unit configured to acquire a three dimensional image of the subject and a direction corresponding to an orientation of the ultrasonic probe;
      a specification unit configured to specify a target point inside the subject in the three dimensional image acquired by the acquisition unit;
      a processor unit configured to identify, as a position on a body surface of the subject, an intersection between a straight line and the body surface of the subject, the straight line extending from the target point to the body surface in a same direction as the direction corresponding to the orientation of the ultrasonic probe; and
      a display controller configured to cause a display unit to display the ultrasonic image acquired by the ultrasonic probe and the identified position on the body surface of the subject superimposed on a body mark image indicating the shape of the body surface of the subject.

2. The image processing apparatus according to claim 1, wherein the processor unit is further configured to determine a direction in which the ultrasonic probe needs to be moved along the body surface of the subject to change the position where the ultrasonic probe captures the ultrasonic image to the identified position based on a difference between the position, measured by a measurement unit, where the ultrasonic probe captures the ultrasonic image and the identified position on the body surface, and
   wherein the display controller causes the display unit to display the determined direction along with the position where the ultrasonic probe captures the ultrasonic image and the identified position on the body surface.

3. The image processing apparatus according to claim 2, wherein the processor unit is further configured to:
   acquire information about a predetermined area of the subject stored in association with a captured portion or patient information, and
   determine a direction in which the ultrasonic probe needs to be moved to detour the predetermined area.

4. The image processing apparatus according to claim 3, wherein the processor unit further identifies an orientation of the ultrasonic probe so that the specified target point falls within an area of the subject where the ultrasonic probe captures the ultrasonic image, and
   wherein the processor unit determines a direction in which the ultrasonic probe needs to be moved to change the orientation of the ultrasonic probe to the identified orientation.

5. The image processing apparatus according to claim 4, wherein the processor unit is further configured to determine whether a distance between the measured position where the ultrasonic probe captures the ultrasonic image and the identified position on the body surface becomes equal to or smaller than a predetermined distance, and
   wherein the display controller causes the display unit to display a direction in which the ultrasonic probe is to be moved to change the orientation of the ultrasonic probe according to a result of the determination.

6. The image processing apparatus according to claim 2, wherein the display controller causes the display unit to display a direction in which the ultrasonic probe is moved along the body surface and to sequentially display the ultrasonic image of the subject captured in a predetermined frame rate by the ultrasonic probe.

7. The image processing apparatus according to claim 1, wherein the processor unit is further configured to:
   acquire information about a predetermined area of a subject stored in association with any of a captured portion or patient information; and identify the position on the body surface so that the identified position on the body surface of the subject is not included in the predetermined area.

8. The image processing apparatus according to claim 3, wherein the captured portion is a breast, and the predetermined area corresponding to the breast is an area based on a nipple.

9. The image processing apparatus according to claim 2, wherein the processor unit further identifies a position on the body surface based on the specified target point inside the subject and the position or the orientation of the ultrasonic probe measured by the measurement unit.

10. The image processing apparatus according to claim 9, wherein the processor unit identifies a target contact-position between the ultrasonic probe and the body surface such that the specified target point falls within the imaging range of the ultrasonic probe with the measured orientation of the ultrasonic probe kept maintained.

11. The image processing apparatus according to claim 1, wherein the processor unit selects and identifies the position on the body surface of the subject from a plurality of candidate positions based on the specified target point inside the subject and based on a state of the ultrasonic probe.

12. The image processing apparatus according to claim 1, wherein the processor unit acquires a plurality of candidate positions on the body surface corresponding to the specified target point inside the subject and identifies the position nearest to the position of the ultrasonic probe out of the candidate positions as the identified position of the body surface to be displayed.

13. The image processing apparatus according to claim 1, wherein the processor unit identifies the position where a distance to the specified target point is smaller than a threshold out of a plurality of positions along the body surface where the specified target point inside the subject is substantially in the normal direction of the body surface as a candidate position of the position on the body surface to be displayed by the display unit.

14. The image processing apparatus according to claim 2, wherein the processor unit determines a direction in which the ultrasonic probe is to be moved along the body surface from the identified position on the body surface to a position on the body surface corresponding to the specified target point inside the subject, based on a relationship between the specified target point and the identified position, and
wherein the display controller causes the display unit to display the position where the ultrasonic probe captures the ultrasonic image, the identified position, and the direction in which the ultrasonic probe is to be moved along the body surface.

15. The image processing apparatus according to claim 1, wherein the display controller superimposes a mark of the position where the ultrasonic image is captured and the identified position of the body surface of the subject on at least one of the body mark image and the three dimensional image, and
wherein the display controller causes the display unit to display the superimposed positions.

16. The image processing apparatus according to claim 15, wherein the acquisition unit is further configured to acquire either a magnetic resonance imaging (MRI) image or a computed tomography (CT) image of the subject as the three dimensional image.

17. An ultrasonic imaging apparatus comprising:
the image processing apparatus according to claim 1;
the ultrasonic probe;
a measurement unit configured to measure a position and an orientation of the ultrasonic probe; and
the display unit.

18. The image processing apparatus according to claim 1, wherein the position on the body surface of the subject is changed when the orientation of the ultrasonic probe is changed.

19. The image processing apparatus according to claim 1, wherein the acquisition unit acquires a position of the ultrasonic probe, and
wherein the position on the body surface of the subject is not changed when the position of the ultrasonic probe is changed.

20. The image processing apparatus according to claim 1, wherein the straight line is a line segment extending opposite to the gravity direction from the target point to the body surface of the subject, and
wherein the orientation of the ultrasonic probe is caused to agree with the gravity direction of the line segment such that the target point is included in a plane represented by the ultrasonic image.

21. An image processing method for controlling a processor coupled to memory storing instructions for supporting imaging performed by an ultrasonic probe which acquires an ultrasonic image of a subject, the image processing method comprising:
acquiring a three dimensional image of the subject and a direction corresponding to an orientation of the ultrasonic probe;
specifying a target point inside the subject in the three dimensional image;
processing using the processor to identify, as a position on a body surface of the subject, an intersection between a straight line and the body surface of the subject, the straight line extending from the target point to the body surface in a same direction as the direction corresponding to the orientation of the ultrasonic probe; and
causing a display controller to display the ultrasonic image acquired by the ultrasonic probe and the identified position on the body surface of the subject superimposed on a body mark image indicating the shape of the body surface of the subject.

* * * * *